(12) United States Patent
Jaürnig

(10) Patent No.: US 6,235,174 B1
(45) Date of Patent: May 22, 2001

(54) GAS SENSOR, IN PARTICULAR FOR DETERMINING THE OXYGEN CONTENT IN EXHAUST GASES OF INTERNAL COMBUSTION ENGINES

(75) Inventor: Udo Jaürnig, Yokohama (JP)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/238,341

(22) Filed: Jan. 27, 1999

(30) Foreign Application Priority Data

Jan. 29, 1998 (DE) .............................................. 198 03 334

(51) Int. Cl.$^7$ ................................................. G01N 27/407
(52) U.S. Cl. ......................... 204/427; 204/426; 205/784.5
(58) Field of Search ..................................... 204/421–429

(56) References Cited

U.S. PATENT DOCUMENTS

| 4,096,050 | * | 6/1978 | Kobayashi et al. | 204/428 |
|---|---|---|---|---|
| 4,362,609 | * | 12/1982 | Sano et al. | 204/428 |
| 4,526,672 | * | 7/1985 | Reed | 204/428 |
| 4,588,494 | * | 5/1986 | Kato et al. | 204/426 |
| 5,246,562 | | 9/1993 | Weyl et al. . | |
| 5,830,339 | * | 11/1998 | Watanabe et al. | 204/428 |

FOREIGN PATENT DOCUMENTS 41 26 378    4/1992 (DE) .

* cited by examiner

*Primary Examiner*—T. Tung
(74) *Attorney, Agent, or Firm*—Kenyon & Kenyon

(57) ABSTRACT

A gas sensor, in particular for determining the oxygen content in exhaust gases of internal combustion engines, is described. The gas sensor includes a sensing element sealedly fastened in a housing, whose segment on the measured gas side has at least one electrode exposed to a measured gas, at least one electrode exposed to a reference gas, and a reference gas conduit, extending in the longitudinal direction of the sensing element, which terminates at the segment of the sensing element remote from the measured gas and is connected to a reference gas source; and having contacts remote from the measured gas for making contact to the electrodes of the sensing element. Provision is made for the reference gas conduit to terminate at a large surface of the sensing element and to be sealed with a planar sealing fit.

18 Claims, 4 Drawing Sheets

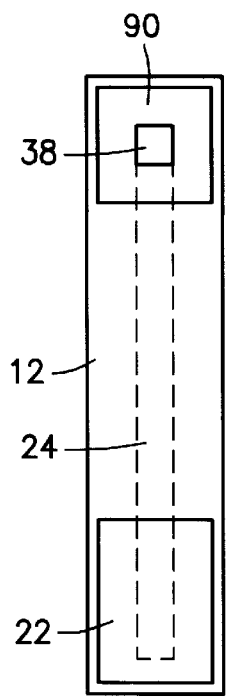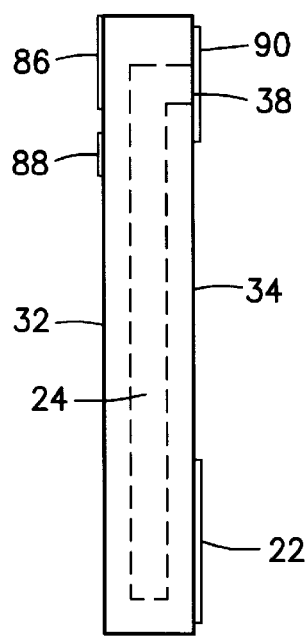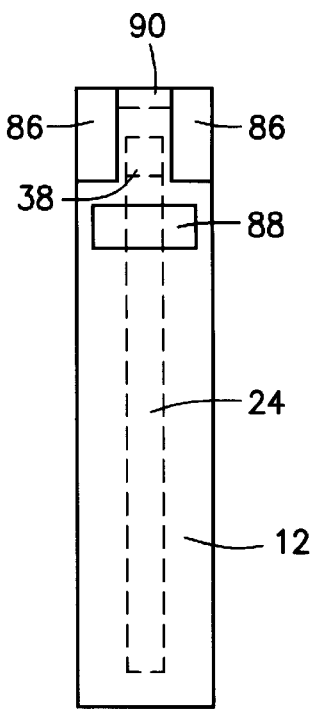
Fig. 8a  Fig. 8b  Fig. 8c
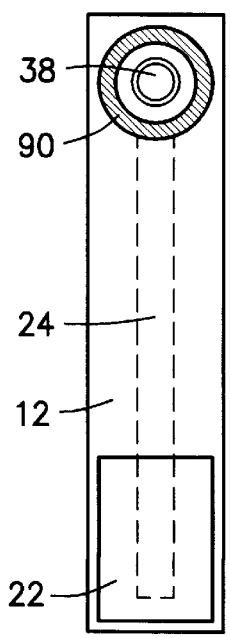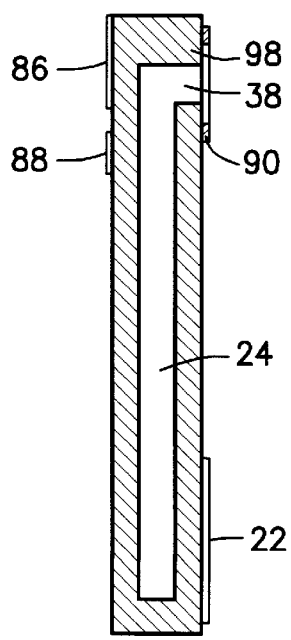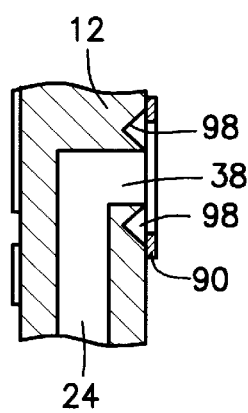
Fig. 9a  Fig. 9b  Fig. 9c

GAS SENSOR, IN PARTICULAR FOR DETERMINING THE OXYGEN CONTENT IN EXHAUST GASES OF INTERNAL COMBUSTION ENGINES

FIELD OF THE INVENTION

The present invention relates to a gas sensor, in particular for determining an oxygen content in exhaust gases of internal combustion engines.

BACKGROUND INFORMATION

A conventional gas sensor includes a sensing element fastened sealedly in a housing. The sensing element is typically configured as a planar sensing element that has a first electrode exposed to a measured gas and a second electrode exposed to a reference gas. In order to deliver a reference gas onto the reference gas electrode, there is provided inside the sensing element a reference gas conduit, running in its longitudinal extension, which can be connected, at an end of the sensing element remote from the measured gas, to a reference gas source, for example the atmosphere. The reference gas conduit terminates at one end surface of the sensing element, and is connected to the reference gas source via a retaining and sealing element of the sensing element that is fastened in a housing of the gas sensor.

For example, German Patent No. 41 26 378 describes a conventional gas sensor. It is disadvantageous in this context that the reference gas conduit terminating at the end face cannot be adequately sealed against possible contaminants. In order to prevent undesired signal falsification, however, the reference gas conduit must be securely sealed against the penetration of substances, for example outside gases, which might falsify the reference gas.

SUMMARY OF THE INVENTION

The gas sensor according to the present invention has an advantage that reliable sealing of the reference gas conduit is possible in a simple fashion. Because the reference gas conduit terminates at a large surface of the sensing element and is sealed with a planar sealing fit, it is easy to achieve hermetic sealing of the reference gas conduit using a planar pressure that is preferably provided. Especially because the reference gas conduit terminates at a large side of the sensing element, a sufficiently large surface surrounding the outlet of the reference gas conduit is available for constituting the planar sealing fit.

In a preferred embodiment of the present invention, provision is made for the reference gas conduit to be sealedly joined to a reference gas guidance element that runs parallel to the sensing element and ends at a side of the gas sensor facing away from the measured gas. The reference gas guidance element very advantageously makes possible a prolongation of the reference gas conduit using a carrier which sealingly retains the sensing element. It is further preferred if a sealing element, preferably of planar configuration, is arranged between the reference gas guidance element and the outlet of the reference gas conduit. A good sealing effect is attained in particular if the sealing element is plastically deformable during assembly of the gas sensor.

In a further preferred embodiment of the present invention, provision is made for the reference gas guidance element simultaneously to provide contacting of at least one of the electrodes of the sensing element. This results in sealed guidance of the reference gas and simultaneously in a sealed passthrough contact to at least one of the electrodes through the retaining element.

In a further preferred embodiment of the present invention, provision is made for the reference gas guidance element to be formed by the retaining element, the retaining element preferably comprising a ceramic shaped element which has the integrated reference gas guidance element. It is thereby possible, with few parts, to combine sealed connection of the reference gas conduit of the sensing element with sealed immobilization of the sensing element in the housing of the gas sensor.

BRIEF DESCRIPTION OF THE DRAWINGS

FIG. 8a shows a view of a sensing element in a first exemplary embodiment.

FIG. 8b shows another view of the sensing element in the first exemplary embodiment.

FIG. 8c shows a further view of the sensing element in the first exemplary embodiment.

FIG. 9a shows a view of a sensing element in a second variant embodiment.

FIG. 9b shows another view of the sensing element in the second variant embodiment.

FIG. 9c shows a further view of the sensing element in the second variant embodiment.

DETAILED DESCRIPTION

Figure 1:
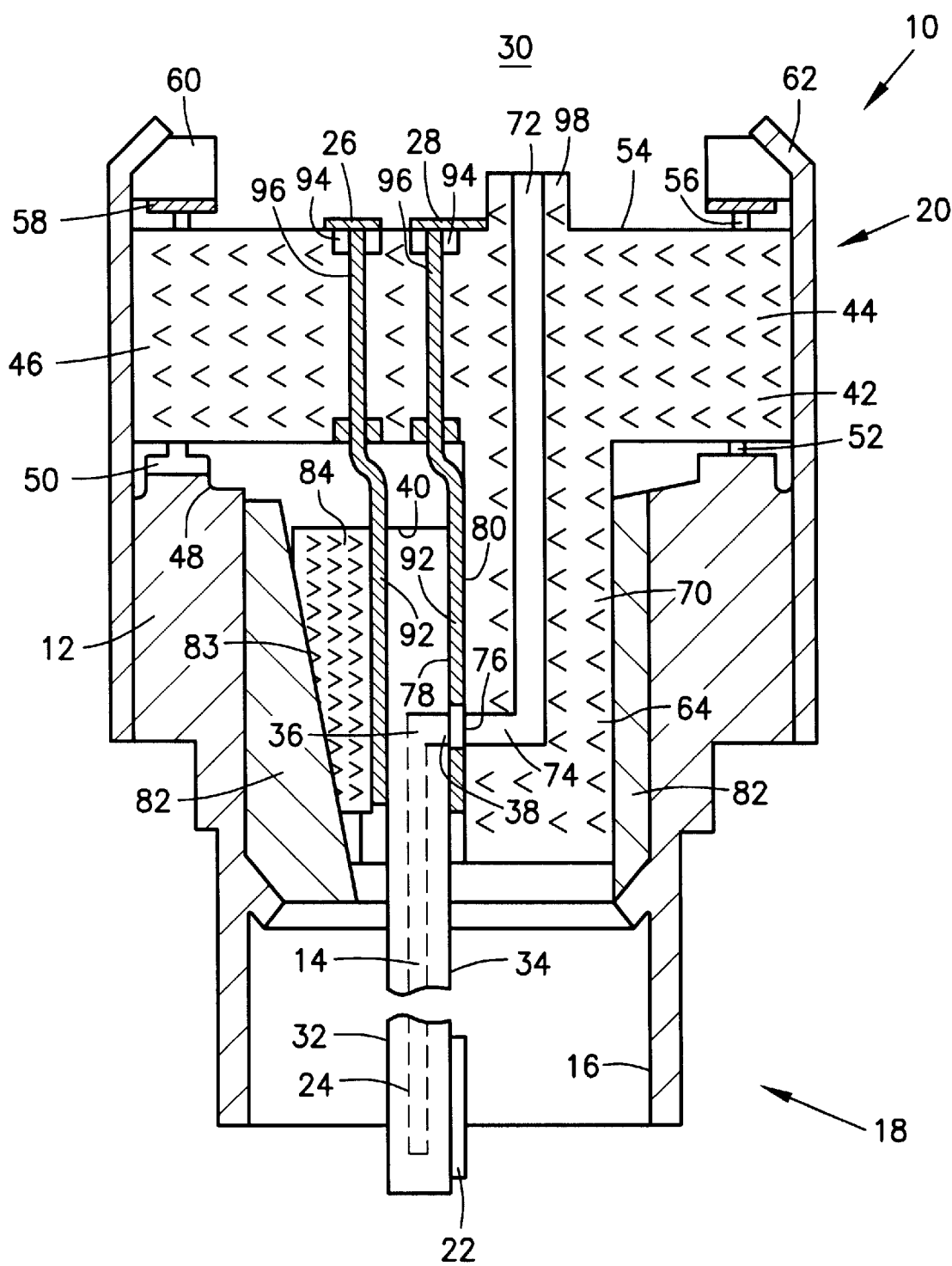
FIG. 1 shows a sectioned depiction of a portion of a gas sensor in a first exemplary embodiment of the present invention.

FIG. 1 shows a partial sectioned depiction of a gas sensor 10, for example for determining the oxygen content in exhaust gases of internal combustion engines. Gas sensor 10 possesses a housing 12 which receives a sensing element 14. The housing is of tubular configuration, and possesses an axially extending passthrough opening 16 into which sensing element 14 extends with its longitudinal extension. Housing 12 is sealedly inserted in a measured gas duct, for example an exhaust gas duct of a motor vehicle. Sensing element 14 projects into the measured gas line so as to give rise to a segment 18 toward the measured gas, and a segment 20 remote from the measured gas, of gas sensor 10. Sensing element 14 is sealedly fastened in housing 12. This means that a hermetic seal exists inside housing 12 between segment 20 remote from the measured gas and segment 18 toward the measured gas. Housing 12 can be fastened to the measured gas line, for example, using a coupling nut, a plug-in flange, or other suitable measures.

Sensing element 14 possesses an electrode 22 exposed to the measured gas and an electrode (not depicted further) exposed to a reference gas. In addition, sensing element 14 can have heating devices (also not depicted further) at its end toward the measured gas. In order to deliver reference gas onto the reference-gas electrode, sensing element 14 possesses along its longitudinal extension an internal reference gas conduit 24. In order for gas sensor 10 to be used as intended, it is necessary both for the electrodes (and, if applicable, the heating device) of sensing element 14 to be connected to connecting contacts 26 and 28 remote from the measured gas, and for reference gas conduit 24 to be connected to a reference gas source 30 remote from the measured gas, for example to atmospheric air. It is necessary in this context that connecting leads of the electrodes of sensing element 14, and reference gas conduit 24 of sensing element 14, be guided in hermetically sealed fashion out of housing 12 to its segment 20 remote from the measured gas.

Sensing element 14 is constituted as a planar sensing element, as will be explained in further detail with reference to FIGS. 8a, 8b, 8c, 9a, 9b, and 9c, resulting in the formation of mutually opposite large surfaces 32 and 34. Reference gas conduit 24 is designed so that, forming a bend 36, it terminates at one of the large surfaces, in the example shown at large surface 34. An outlet 38 of reference gas conduit 24 is thus arranged at an angle of preferably 90 degrees to the longitudinal extension of sensing element 14. Outlet 38 possesses a relatively large spacing from an end face 40, remote from the measured gas, of sensing element 14, so that outlet 38 is surrounded by a relatively large area of large surface 34.

A ceramic shaped element 42, which constitutes a retaining element 44 for sensing element 14, is inserted into housing 12. For this purpose, ceramic shaped element 42 possesses firstly a cylindrical base segment 46 whose outside diameter is adapted to the inside diameter of housing 12 in the region of base segment 46. Ceramic shaped element 42 can thus be inserted into housing 12 with zero clearance. Housing 12 constitutes an annular step 48 at which passthrough opening 16 transitions into a smaller-diameter segment. Annular step 48 receives a first seal element 50, for example an annular seal, on which ceramic shaped element 42 is braced with an annular sealing edge 52. Ceramic shaped element 42 has on its end surface 54 remote from the measured gas a further annular sealing edge 56 with which a further sealing element 58, for example a sealing ring, is associated. Sealing element 58 is in surface contact with a contact pressure element 60 which, by crimping over of an upper rim segment 62 of housing 12, can have applied to it an axial force acting toward passthrough opening 16. As a result, using contact pressure element 60, ceramic shaped element 42 is pressed with its base segment 46 against annular step 48 of housing 12 and thus immobilized. A hermetically sealed arrangement of ceramic shaped element 42 in housing 12 is achieved using sealing elements 50 and 58 in conjunction with sealing edges 52 and 56.

Figure 2A:
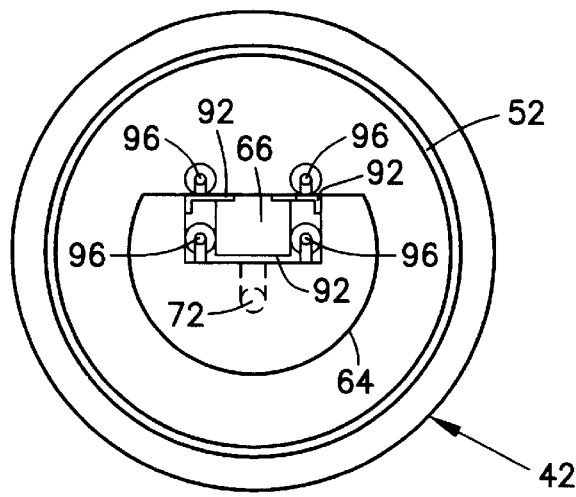
FIG. 2a shows a bottom view of a ceramic shaped element.
Figure 2B:
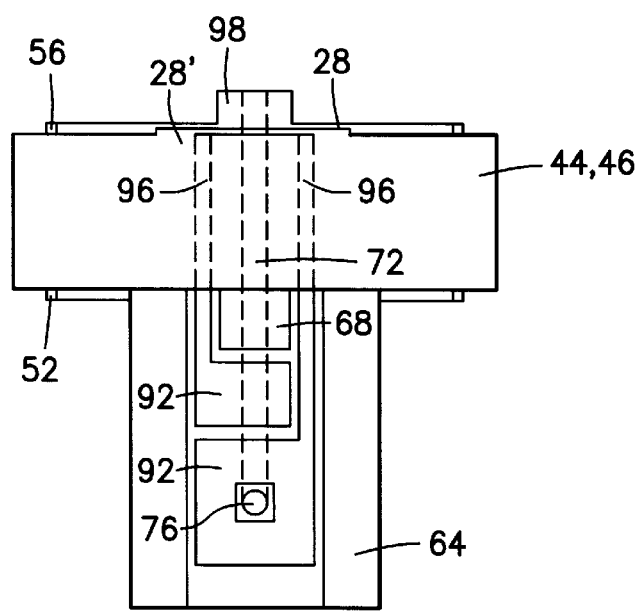
FIG. 2b shows a side view of the ceramic shaped element.
Figure 2C:
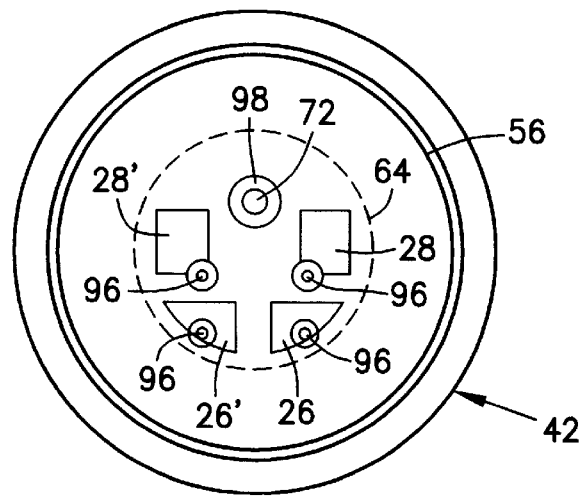
FIG. 2c shows a plan view of the ceramic shaped element.

Ceramic shaped element 42 possesses an axially extending extension 64 which—as illustrated in even more detail by the views of FIGS. 2a, 2b and 2c—has a partially cylindrical geometrical configuration. Extension 64 constitutes a receptacle 66 for sensing element 14. Receptacle 66 (FIG. 2a) is constituted as an axially extending groove whose dimensions are adapted to the dimensions of the planar sensing element 14. Receptacle 66 possesses an axial length such that when sensing element 14 is set in place up to a stop 68, outlet 38 of reference gas conduit 24 is overlapped by extension 64 of ceramic shaped element 42.

Ceramic shaped element 42 moreover simultaneously constitutes a reference gas guidance element 70 for sealed connection of reference gas conduit 24 of sensing element 14 to reference gas source 30. For this purpose, ceramic shaped element 42 possesses a conduit 72, extending parallel to reference gas conduit 24, which terminates via a bend 74 in receptacle 66 of extension 64. An outlet 76 of conduit 72 thereby aligns with outlet 38 of reference gas conduit 24. A continuous connection is thus created from reference gas source 30 via conduit 72 and reference gas conduit 24 to the electrode of sensor element 14 on the measured gas side that is exposed to the reference gas. A sealing fit between reference gas conduit 24 and conduit 72 is formed by one of the opposing surfaces 78 of sensing element 14 and 80 of ceramic shaped element 42. In order to achieve a high surface pressure and thus a good sealing effect between surfaces 78 and 80, extension 64 of ceramic shaped element 42 is surrounded by a locking ring 82 which on the one hand rests conformingly against extension 64 and constitutes a conical recess 83 located opposite receptacle 66.

A locking wedge 84 adapted to the conicity of recess 83 and made of an insulating material is inserted into recess 83. As a result of axial insertion of locking wedge 84 into recess 83, sensing element 14 has applied to it a radially acting force which effects a surface pressure between surfaces 78 and 80 that results in a sealed connection between reference gas conduit 24 and conduit 72.

Connecting contacts 86, 88 and 90 (FIGS. 8a, 8b, 8c, 9a, 9b and 9c) arranged on sensing element 14, which provide electrical contact to the electrodes and to a heating device of sensing element 14, are patterned on large surfaces 32 and 34 of sensing element 14. These are connected in electrically conducting fashion, via conductor paths (not depicted individually), to the heating device and the electrodes, respectively. Connecting contacts 86, 88, 90 are of substantially planar configuration, and are arranged in the region of sensor element 14 which lies inside recess 66 of ceramic shaped element 42. In this context, one connecting contact 90 fits around outlet 38 of reference gas conduit 24 and simultaneously constitutes the sealing surface (surface 78) of the sealing fit between sensing element 14 and ceramic shaped element 42.

Electrical connecting leads 92, which on the one hand are in surface contact with connecting contacts 86, 88, 90 and are passed via passthrough contacts 96 through base segment 46 of ceramic shaped element 42, are provided in order to connect the external connecting contacts 26 and 28 of gas sensor 10 to connecting contacts 86, 88 and 90 of sensing element 14. Seals 94 are provided for the hermetically sealed passage of passthrough contacts 96. Secure electrical contact to sensing element 14 is also accomplished by axial displacement of locking wedge 84 into recess 82, so that electrical connecting leads 92 are pressed radially against connecting contacts 86, 88 and 90. Sealed connection of reference gas conduit 24 to conduit 72 is thereby combined with simultaneous electrical contact to sensing element 14.

All in all, it is thereby possible, with a few shaped parts that are of simple construction and can thus easily be appropriately manufactured by mass production, to achieve hermetically sealed immobilization of sensing element 14 in housing 12 of gas sensor 10.

A radially acting contact force or sealing force applied via locking wedge 84 can be selected to be such magnitude that electrical connecting contacts 86, 88, 90, which are usually made of platinum or gold, are slightly plastically deformed, so that in addition to secure electrical contacting, the sealing effect between outlets 38 of reference gas conduit 24 and 76 of conduit 72 is improved. The overall result is thus reliably to prevent the penetration into reference gas conduit 24 of substances that falsify the reference gas.

In order to connect gas sensor 10 to an analysis circuit (not depicted), a plug can be clamped onto a collar (not depicted) of housing 12, contact pins of the plug coming into contact with external connecting contacts 26 and 28. In order to prevent mispolarity, a collar 98 which surrounds conduit 72 in shoulder fashion is configured on end surface 54 of ceramic shaped element 42. It is thereby possible, very advantageously, to integrate into the contact plug of the analysis circuit a reference gas guide which must surround collar 98 for mutual mispolarity-protected insertion of the connecting plug.

In order further to improve a sealing effect between outlets 38 of reference gas conduit 24 and 76 of conduit 72, outlet 38 can be surrounded by a sealing edge 98, as illustrated by the views of sensing element 14 in FIGS. 9a through 9c. Sealing edge 98 can, for example, be achieved by embossing sensing element 14 prior to sintering.

Ceramic shaped element 42 is shown in a variety of views in FIGS. 2a through 2c, FIG. 2a depicting a bottom view, FIG. 2b a side view, and FIG. 2c a plan view (corresponding to the position shown in FIG. 1). Parts identical to those in FIG. 1 are given identical reference characters and are not explained again. The compact and multifunctional construction of ceramic shaped element 42 will be made clear by reference to the views of FIGS. 2a through 2c. In addition to immobilization of sensing element 14 via base segment 46, contact is made to sensing element 14 in accordance with receptacle 66, and simultaneously a seal is accomplished between conduit 72 and reference gas conduit 24 of sensing element 14.

Figure 3:
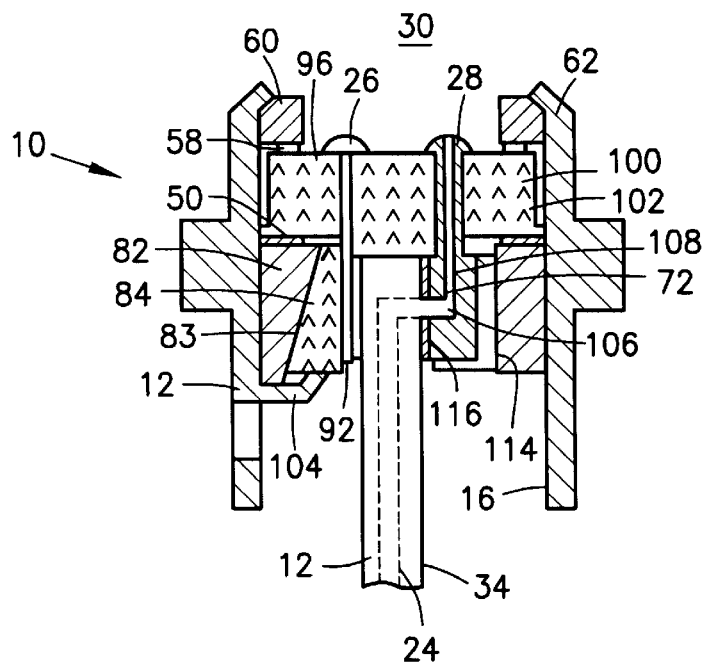
FIG. 3 shows a sectioned depiction of the gas sensor in a second exemplary embodiment of the present invention.

FIG. 3 shows, in a partial sectioned depiction, a further embodiment of a gas sensor 10. Parts identical to those in FIG. 1 are given identical reference characters and are not explained again, so that to this extent only the differences which exist will be discussed.

Sensing element 14 is once again fixed in position via a ceramic shaped element 100 which constitutes a retaining element 102. Retaining element 102 possesses an outside diameter which is adapted to the inside diameter of housing 12, so that the latter can be introduced with zero clearance into passthrough opening 16 of housing 12. Housing 12 has at least one cantilever arm 104, pointing radially inward, which serves (in a manner yet to be explained) as a buttress.

Sensing element 14 possesses the configuration already explained with reference to FIG. 1 and FIGS. 8a, 8b, 8c, 9a, 9b and 9c. To connect reference gas conduit 24 to reference gas source 30, a reference gas guidance element 106, which in turn constitutes conduit 72, is provided. In contrast to the exemplary embodiment shown in FIG. 1, reference gas guidance element 106 is not a component of ceramic shaped element 100, but rather is configured as a separate shaped element 108 made of an electrically conducting material. This is passed sealedly through a passthrough opening 110 of ceramic shaped element 100 and simultaneously constitutes connecting contact 28. Because reference gas guidance element 106 possesses electrical conductivity, it not only ensures sealed connection of reference gas conduit 24 to reference gas source 30 via conduit 72, but simultaneously serves as electrical connecting lead 112 of electrical connecting contact 90 (FIGS. 8a, 8b, 8c, 9a, 9b and 9c) of sensing element 14.

Assembly of the gas sensor is accomplished by introducing into housing 12 a locking ring 82 in whose conically profiled is recess 83 locking wedge 84 is arranged. Locking wedge 84 is made of an electrical insulating material, so that any electrically conducting connection between electrical connecting lead 92 and locking ring 82 is prevented. Reference gas guidance element 106 is equipped with an insulating cap 114, so that electrical contact between locking ring 82 and reference gas guidance element 106, which simultaneously serves as electrical connecting lead 112, is also impossible.

Locking ring 82 and locking wedge 84 are mutually compressed by applying an axially acting force on ceramic shaped element 100 via contact pressure element 60 by crimping over rim segment 62 of housing 12, so that as a result of conical recess 83, a radially acting force is exerted on sensing element 14. The result is on the one hand to create secure contacting between the connecting contacts of sensing element 14 (FIGS. 8a, 8b, 8c, 9a, 9b and 9c) and electrical connecting leads 92 and 112, and to constitute a planar sealing fit between large surface 34 of sensing element 14 and reference guidance element 106. In order to enhance the sealing effect of this planar sealing fit, a sealing element 116, for example in the form of a plastically deformable, electrically conducting seal and contact layer, can be applied between sensing element 14 and reference gas guidance element 106. This layer is plastically deformed along with locking wedge 84 as locking ring 82 is compressed, so that a considerable sealing effect is attainable. This sealing element can be made, for example, of a heat-resistant copper, nickel, iron, or noble metal solder. These materials are temperature-resistant up to a temperature of more than 700 degrees C., so that they are suitable as sealing materials when acted upon by relatively high heat, as is generally present at the installation location of the gas sensor in motor vehicles. In addition, any irregularities existing, as a function of production engineering, between sensing element 14 and reference gas guidance element 106 can be compensated for by sealing element 116. Compensation is also possible for different coefficients of thermal expansion of the materials of gas sensor 10, especially in the region of the planar sealing fit.

In addition to integration of the electrical connection between connecting contact 90 of sensing element 14 and external connecting contact 28, and the creation of a sealed connection between reference gas conduit 24 and reference gas source 30 via reference gas guidance element 106, its eccentric arrangement on ceramic shaped element 100 simultaneously guarantees correct polarity for a contact plug (not depicted) connecting gas sensor 10 to an analysis circuit.

Figure 4:
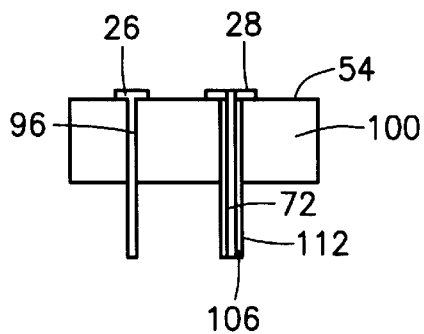
FIG. 4 shows a schematic partial view of an exemplary embodiment of the retaining element illustrated in FIG. 1 according to the present invention.
Figure 5:
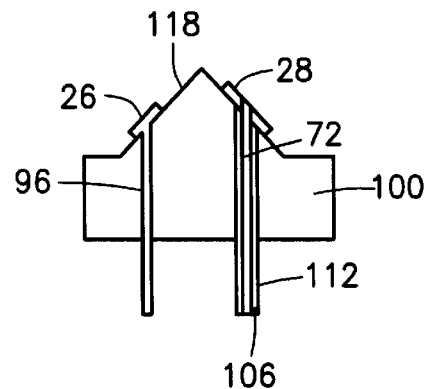
FIG. 5 shows a schematic partial view of another exemplary embodiment of the retaining element illustrated in FIG. 1 according to the present invention.
Figure 6:
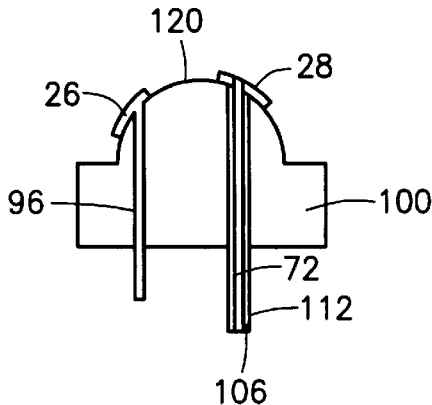
FIG. 6 shows a schematic partial view of a further exemplary embodiment of the retaining element illustrated in FIG. 1 according to the present invention.
Figure 7:
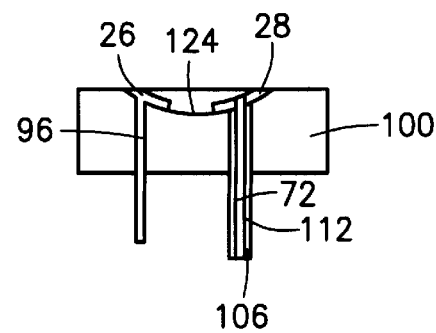
FIG. 7 shows a schematic partial view of yet another exemplary embodiment of the retaining element illustrated in FIG. 1 according to the present invention.

As illustrated by the detail views in FIGS. 4 through 7, ceramic shaped element 100 can have geometrical features on its end surface 54. FIG. 4 schematically illustrates the arrangement, shown in FIG. 3, of ceramic shaped element 100 with a flat end surface 54 on which connecting contacts 26 and 28 are arranged. According to FIG. 5, end surface 54 can have a conical elevation 118 on whose enveloping surfaces the electrical connecting contacts 26 and 28 are arranged. Conical elevation 118 makes it possible to enlarge the area of connecting contacts 26 and 28, and thus enhance contact reliability with a contact plug that can be connected to gas sensors 10. The same result is achieved with a convex elevation 120 as shown in FIG. 6, or a concave depression 122 as shown in FIG. 7. In addition to enlarging the contact areas of contacts 26 and 28, the geometrical features on end surface 54 can at the same time implement a positive and nonpositive connection to the connecting plug of the analysis circuit, thus making possible, in easy fashion, secure contacting to gas sensor 10.

Aluminum oxide $Al_2O_3$ is suitable, for example, for the implementation of ceramic shaped elements 42 (FIG. 1) or 100 (FIG. 3); hermetically sealed passage of passthrough contacts 96 and reference gas guidance elements 106 can be accomplished by soldering, for example active soldering, or eutectic bonding of the electrically conductive materials, which for example are made of copper, into ceramic shaped elements 42 and 100.

The use of hermetically sealed ceramic shaped elements 42 or 100 makes possible contacting between sensing element 14 and a connecting plug without placement of a wiring harness associated with gas sensor 10. In addition to simplified assembly, the specific properties of the ceramic shaped elements, of the hermetic passthrough contacts, and of the sealing of reference gas conduit 42 using a planar sealing fit, allow the sealing of the entire arrangement to be improved as compared with known gas sensors.

What is claimed is:

1. A gas sensor, comprising:
   a housing;
   a sensing element sealedly coupled in the housing, the sensing element including a segment portion and a reference gas conduit, the segment portion being situated on a measured gas side of the housing, the segment portion has been added after including at least one first electrode which is exposed to a measured gas and at least one second electrode which is exposed to a reference gas, the reference gas conduit extending in a longitudinal direction of the sensing element and terminating at a second segment portion remote from the measured gas, the reference gas conduit being connected to a reference gas source, the reference gas conduit terminating at an outlet at a longitudinal side surface of the sensing element and is sealed with a planar sealing fit, the longitudinal side surface extending in the longitudinal direction of the sensing element; and
   first contacts situated at a second predetermined distance from the measured gas, the first contacts being adapted to be electrically connected to the at least one first electrode and the at least one second electrode.

2. The gas sensor according to claim 1, wherein the gas sensor is utilized to determine an oxygen content in an exhaust gas of an internal combustion engine.

3. The gas sensor according to claim 1, further comprising:
   a ceramic shaped element immobilizing the sensing element in the housing and forming a reference gas guidance element.

4. The gas sensor according to claim 3, wherein the ceramic shaped element includes a conduit which connects the reference gas conduit to the reference gas source via the outlet at the longitudinal side surface of the sensing element, the conduit being sealed with the reference gas conduit via the planar sealing fit.

5. The gas sensor according to claim 4, wherein the conduit is integrated into the ceramic shaped element.

6. The gas sensor according to claim 4, wherein the ceramic shaped element constitutes a receptacle for the sensing element, the outlet of the reference gas conduit and an outlet of the conduit of the ceramic shaped element are opposite to one another inside of a recess.

7. The gas sensor according to claim 6, wherein at least one of the reference gas conduit outlet and the ceramic shaped element conduit outlet is surrounded by a sealing edge.

8. The gas sensor according to claim 4, wherein the ceramic shaped element has geometrical features to ensure a correctly polarized contacts of the first contacts of the sensor.

9. The gas sensor according to claim 8, wherein the geometrical features include a collar surrounding the conduit.

10. The gas sensor according to claim 3, wherein the sensing element is retained in a surface contact with the ceramic shaped element via a compressive force which acts radially to the longitudinal extension of the sensing element.

11. The gas sensor according to claim 10, further comprising:
    a locking ring surrounding an extension of the ceramic shaped element to apply the compressive force, the ceramic shaped element forming a receptacle; and
    a locking wedge for compressing the locking ring.

12. The gas sensor according to claim 3, further comprising:
    a plastically deformable sealing element situated between the sensing element and one of the ceramic shaped element and a shaped element, at least at the outlet at the longitudinal side surface of the sensing element and at an outlet region of the one of the ceramic shaped element and the shaped element.

13. The gas sensor according to claim 12, wherein the shaped element is of an electrically conductive material.

14. The gas sensor according to claim 3, wherein the ceramic shaped element includes a pressure-tight passthrough contact, a connecting contact of the sensing element being coupled to the at least one of the first contacts of the sensor using the pressure-tight passthrough contacts.

15. The gas sensor according to claim 3, wherein the first contacts of the sensor are situated on an end surface of the ceramic shaped element.

16. The gas sensor according to claim 15, wherein the end surface has geometrical features to enlarge an available contact area of the first contacts of the sensor.

17. The gas sensor according to claim 1, further comprising an electrically conductive shaped element including a conduit connecting the reference gas conduit to the reference gas source, the shaped element providing an electrical contacting to a connecting contact of the sensing element.

18. The gas sensor according to claim 1, wherein the outlet at the longitudinal side surface of the sensing element meets a second conduit.

* * * * *

UNITED STATES PATENT AND TRADEMARK OFFICE
CERTIFICATE OF CORRECTION

PATENT NO. : 6,235,174 B1
DATED : May 22, 2001
INVENTOR(S) : Jaürnig, Udo

It is certified that error appears in the above-identified patent and that said Letters Patent is hereby corrected as shown below:

Column 6,
Line 7, change "profiled is recess" to -- profiled recess --

Column 7,
Line 33, change "has been added after" to -- situated on the measured gas side of the housing --

Signed and Sealed this

Twelfth Day of November, 2002

*Attest:*

*Attesting Officer*

JAMES E. ROGAN
*Director of the United States Patent and Trademark Office*